United States Patent [19]

Liu

[11] Patent Number: 5,071,839

[45] Date of Patent: Dec. 10, 1991

[54] SAFE PHARMACEUTICAL COMPOSITION FOR DECREASING SIDE EFFECTS OF ANTIVIRAL DRUGS AND INCREASING THE IMMUNE FUNCTION (SDI) II

[76] Inventor: Yaguang Liu, 67-08 168th St., Flushing, N.Y. 11365

[21] Appl. No.: 115,872

[22] Filed: Nov. 2, 1987

[51] Int. Cl.⁵ .................... A61K 31/70; A61K 31/765
[52] U.S. Cl. ........................................ 514/25; 514/26; 514/54
[58] Field of Search .............................. 514/25, 26, 54

[56] References Cited

U.S. PATENT DOCUMENTS 4,675,318  6/1987  Liu ...................................... 514/215
4,684,628  8/1987  Liu ........................................ 514/26

Primary Examiner—John W. Rollins

[57] ABSTRACT

The new safe pharmaceutical composition (SDI II) and processes are provided for decreasing side effects of antiviral drugs and increasing the immune function.

The pharmaceutical composition is composed of two ingredients: Polysaccharides of Wang Qi and Ginsenoside. The SDI II is nontoxic.

2 Claims, No Drawings

SAFE PHARMACEUTICAL COMPOSITION FOR DECREASING SIDE EFFECTS OF ANTIVIRAL DRUGS AND INCREASING THE IMMUNE FUNCTION (SDI) II

BACKGROUND OF THE INVENTION

1. Field of the Invention

The present invention related to new pharmaceutical composition for decreasing side effects of antiviral drugs and increasing the immune function.

2. Description of Prior Art

U.S. Pat. No. 4,684,628 disclosed that a new pharmaceutical composition for treatment and prevention of cardiovascular disease and increasing immune function contains Ginsenoside, Ophiopogonin, Sesquicarene and Chamigrene. U.S. Pat. No. 4,687,761 disclosed that a new pharmaceutical composition for treatment and prevention of side effects of anticancer chemotherapy and radiotherapy and increasing the immune function contains Ferulic acid, Ginsenoside, Anethole and sodium Cinnamate. U.S. Pat. No. 4,675,318 disclosed that a new pharmaceutical composition for treating nonlymphatic leukemia, such as granulocytic and monocytic leukemia comprising Harringtonine, Homoharringtonine, Anethole, Oleanolic acid and Ginsenoside and method of making the same.

SUMMARY OF THE INVENTION

A new, safe pharmaceutical composition in accordance the present invention for decreasing side effects of antiviral drugs and increasing the immune function which comprises two ingredients, namely Polysaccharide of Wang Qi and Ginsenoside and method of making same.

DETAILED DESCRIPTION

Viruses are enormously important as causative agents of human disease. Virus infections also remain an important source of human mortality. In especial, human T-lymphotropic virus type III (HTLV-III)/lymphadenopathy-associated virus (LAV) is newly discovered retrovirus etiologically linked to acquired immunodeficiency syndrome (AIDS) and AIDS-related disorders. The treatment of AIDS with antiviral drug has recently become critical importance. However, the development of antiviral drug for the treatment of infections viral diseases has progressed very slowly now.

The reason is very difficult to find drug active against virus multiplying within cells that are not also toxic to the same cells. Toxicity is a major problem with all anti-virus drugs because they are not selective enough and therefore may inferfere with normal cellular enzymes and DNA synthesis. For example, 3'-Azido-3'-deoxythymidine (AZT) -the only drug be used against AIDS now - is so toxic that close to half the more seriously ill AIDS patients can not take it. The risk of AZT is very high. AZT decreases in the total white blood count, directly decreases the number of T cells and hemotocrit drops in the patients. Used improperly, the AZT could easily hasten rather than postpone, a patient's death, in especial, AZT can causing late drug toxicity with drug-induced immunosuppression. Serious side-effects of AZT is unavoidable because AZT is blocker of DNA synthesis. AZT is analogue of thymidine. The 3'-substitution makes subseguent 5' to 3'-phosphodiester linkages impossible (chain terminator of DNA synthesis). The accumulation of AZT within cells causes substantial depression of thymidine triphosphate, resulting in bone-marrow suppression and megaloblastic anemia, and decreasing total white blood cells.

The other major antiviral drugs—for example, experimental anti-HTLV III/LAV drug: Ribavirin (Ribofuranosyl-Trazole-Carboxamide), 2',3'-Dideoxycytidine (DDC), 2',3'-Dideoxyadenoside (DDA); anti-Herper virus drug: Idoxuridine (IDU), Vidarabine (Ara-a), Acyclovir (Acycloguanoside, ACV), Cytarabine (Ara-C); anti-leukemia drug (some leukemia cause by retrovirus): Cyclophosphamide (C.P), Cyclocytidine (C.C.), Cytarabine (Ara-C), 5'-Azacytidine (AZC), 6-Azauridune (AZU), 5'-Aza-2'-deoxycytidine (AZCdR); anti-Respriratory rivus drug: Ribavarin et al—have various degree side effects: bone-marrow suppression, megaloblastic anemia and recreasing total white blood cells. Sometime a double-blind controlled study indicated a higher degree of morbidity in antiviral drug-treated patients than in those who received placebo, because the immunosuppressive effects of some antiviral drug outweighed its antiviral activity.

On the other side, certain viruses cause disease depends on an how the host immune responds to a viral infections. In fact, many individuals with healthy immune function could control the viruses without the infections effects that occur with the disease. Viral infection tends to cause disease only in individuals whose immune function have been severely weakened. Considerations such as these provide a ratidnale for immnostimulatory therapy in combination with antiviral chemotherapy.

For reasons given above, one pharmaceutical composition which has two pharmacological functions—decreasing side effects of antiviral drug and increasing immune funtion at same time—is very important and possesses special clinic value for viral infections disease.

As mentioned above, U.S. Pat. No. 4,684,628 and U.S. Pat. No. 4,687,761, which were invented by Ya Guang Liu who is inventor of the present invention, disclosed that Ginsenoside can increase immune function and also Ginseng is regarded by F.D.A. of U.S. as recognized as safe. Wang Qi also is chinese food and very safe. The Ginsenoside has the following chemical structure:

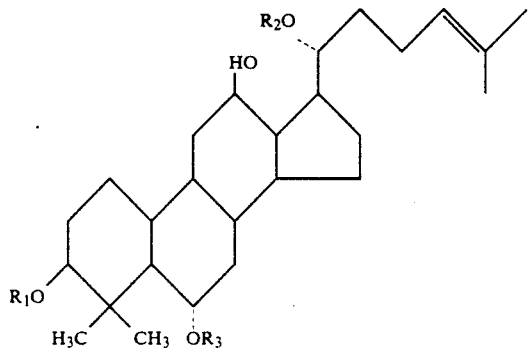

when
$R_1$ = glucose 2→1 glucose
$R_2$ = glucose 6→1 glucose
$R_3$ = H.
The compound is ginsenoside $Rb_1$.
Melting Point: 197°–198° C.
$[\alpha]_D^{22}$ methanol: +12.42.

Properties: White powder (EtOH-BuOH 1:1).
Formula: $C_{54}H_{92}O_{23}$ ($3H_2O$).
when
  $R_1$ = glucose 2→1 glucose
  $R_2$ = Glucose 6→1 arabinose
  $R_3$ = H.
The compound is ginsenoside $Rb_2$.
Melting Point: 200°–203° C.
$[\alpha]_D^{22}$ methanol: +3.05
Properties:: White powder (EtOH-BuOH 1:5)
Formula: $C_{53}H_{90}O_{22}$ ($4H_2O$)
when
  $R_1$ = glucose 2→1 glucose
  $R_2$ = glucose 6→1 arabinose
  $R_3$ = H.
The compound is ginsenoside Rc.
Melting Point: 199°–201° C.
$[\alpha]_D^{22}$ methanol: +1.93
Properties: White powder (EtOH-BuOH 1:5)
Formula: $C_{53}H_{90}O_{22}$
when
  $R_1$ = glucose 2→1 glucose
  $R_2$ = glucose
  $R_3$ = H.
The compound is ginsenoside Rd.
Melting Point: 206°–209° C.
$[\alpha]_D^{22}$ methanol: +19.38
Properties: White powder (EtOH-BuOH 1:1)
Formula: $C_{48}H_{92}O_{18}$
when
  $R_1$ = H
  $R_2$ = glucose
  $R_3$ = glucose 2→1 rhamnose.
The compound is ginsenoside Re.
Melting Point: 201°–203° C.
$[\alpha]_D^{22}$ methanol: −1.00
Properties: colorless needles (50% EtOH)
Formula: $C_{48}H_{92}O_{18}$
when
  $R_1$ = H
  $R_2$ = H
  $R_3$ = glucose 2→1 glucose.
The compound is ginsenoside Rf.
Melting point: 197°–198° C.
$[\alpha]_D^{22}$ methanol: +6.99
Properties: White powder (acetone)
Formula: $C_{42}H_{72}O_{14}$
when
  $R_1$ = H
  $R_2$ = glucose
  $R_3$ = glucose.
The compound is gensenoside $Rg_1$.
Melting point: 194°–196° C.
$[\alpha]_D^{22}$ pyridine: +32
Properties: colorless needles (BuOH)
Formula: $C_{42}H_{72}O_{14}$ ($2H_2O$)
when
  $R_1$ = H
  $R_2$ = H
  $R_3$ = glucose 2→1 rhamnose.
The compound is ginsenoside Rg.
Melting Point: 187°–189° C.
$[\alpha]_D^{22}$ methanol: +5.00–6.00
Properties: colorless needles (EtOH)
Formula: $C_{42}H_{72}O_{13}$
Ro has the following structure:

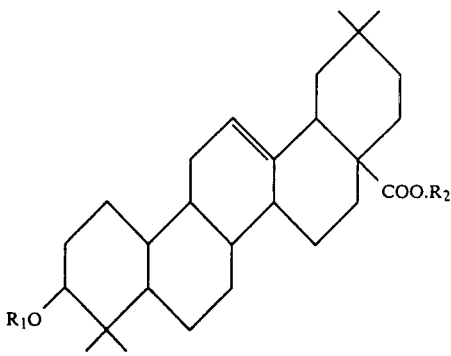

When
  $R_1$ = glucuronic acid 2→1 glucose and
  $R_2$ = glucose
Melting Point: 239°–241° C.
$[\alpha]_D^{22}$ methanol: +15.33
Properties: Colorless needles (methanol)
Formula: $C_{48}H_{76}O_{19}$ ($2H_2O$).

The following specific examples will provide detailed illustrations of methods of producing SDI according to the present invention and pharmaceutical dosage units containing SDI II. Moreover, examples will be given of pharmaceutical testing performed with SDI II. These examples are not intended, however, to limit or restrict the scope of the invention in any way, and should not be construed as providing conditions, parameters, reagents, or starting materials which must be utilized esclusively in order to practice the present invention.

EXAMPLE 1

Extraction of Ginsenoside 2,000 ml of 95% ethanol was added to 1,000 g of dried powder of ginseng derived from Panax quinquefolium L or Panax ginseng C. A. Mey. and allowed to stand for one day at room temperature. The solution was filtered and the extract filtrate saved. 2,000 ml of ethanol was added to the residue and refluxed in a water bath for 6 hours. The reflusing was repeated twice by collecting the ethanol, replacing it with an equal volume of fresh 95% ethanol and refluxing for 6 hours. The refluxed alcohol was cooled and filtered and the filtrate combined with the extract filtrate. Ethanol was then recovered by reduced pressure distillation and the residue dissolved in 500 ml of distilled water. The lipid component was removed with 5 changes of ether by adding 500 ml to the water phase for each extraction. An equal volume of water-saturated butanol was added to the final water phase and the butanol was then distilled under reduced pressure. The residue powder was dissolved in 500 ml of ethanol and 2,000 ml of acetone was added to the ethanol with constant stirring while a precipitate formed. The precipitate was washed twice each with acetone and ether and dried. The resulting white or light yellow powder was the final product, i.e., ginsenosdie.

EXAMPLE 2

Extraction of Polysaccharides of Wang Qi

The roots of *Astragalus membranaceus* Bge, *Astragalus chrysopterus* Bge or other species of Astralus dried and powdered.

3,000 ml of water was added to 1,000 g of dry powder. The solution was heated to boil and simmered two hours after boiling. This water extraction was repeated once and the two extracts combined and filtered. The filtrate was concentrated under reduced pressure to approximately 500 ml and 95% ethanol was added to the concentrate to a final ethanol concentration of 60%. The solution was filtered and the precipitate dissolved in an appropriate amount of water, filter to remove the residue and filtrate saved. The filtrate was concentrated under reduced pressure to 500 ml and 95% ethanol added to the concentrate to a final ethanol concentration of 40-60%. The solution was filtered and the precipitate dissolved in water. The water solution was dialyzed against running water. Dialyzate was concentrated under reduced pressure and 95% ethanol was added to the concentrate to a final ethanol concentration of 80%. The solution was allowed to stand at 4° C. overnight. The supernatant was then discard and the precipitate washed three times with 95% ethanol and then twice with acetone and ether consecutively. The product was vacuum dried.

EXAMPLE 3

Preparation of fine product of SDI II

Fine SDI II preparation according to the present invention consists of:

|  | Weight Percent |
| --- | --- |
| Polysaccharides of Wang Qi | 20 to 80% |
| Ginsenoside | 20 to 80% |

The dry ingredients or derivate of ingredients prepared in accordance with the present invention, may be incorporated tablets, capsules, surups or other form by conventional method.

The tablets can be prepared by mixing the SDI II with suitable binders, excipients, disintegration agents, lubricants and sweetness. Examples of widely used, pharmaceutical acceptable tablet ingredients are corn starch or gelatin as binders, dicalcium phosphte as an excipients, corn starch, potato starch or alginic acid and disintegration agents, magnesium stearate as a lubricant, and sucrose or lactose as sweetening agents. The tablets may be coated with shellac or sugar to facilitate swallowing. The preferred weight ranges of the components in the SDI II tablets are the same as given above for capsule dosage forms. The most preferred weight valued for the components are, as in the case of capsules, 50-100 mg of dry ingredients per dosage unit.

Elixirs or syrups may be prepared by dissolving SDI II in a mixture of water or ethanol and, if desired, adding a sweetener such as sucrose, a suitable preservative, a dye (chosen according to the desired coloration) and a flavoring agent, such as an orange or cherry flavor. The concentration ranges of the SDI II components per teaspoon (5 milliliters) of syrup are the same as given above for capsule and tablet dosage units.

Immunological effects of some Polysaccharide of Astragalus have limitary. For example, Polysaccharide of Astragalus mongholicus Bunge (Astragalan I or II) inhibited the response spleen cells against sheep red blood cells. However, response spleen cells against sheep red blood cells is general and primary immune responses. (Barbara B. Mishell and Stanley M. Shiigi "Selected Methods in Cellular Immundogy" pp 28-37 by W. H. Freeman and Company 1980). Virus infections, Bacterial infections, Chronic stress et al, can decrease above immune responses. In other words, inhibited the response spleen cells against sheep red blood cells be mean by inhibiting capability of destruction of viruses and bacteria. It is worse properties. Ginsenoside together with Polysaccharide of Wang Qi, however, overcome above worse properties. Therefore, ginsenoside together with Polysaccharide of Wang Qi more better than single Polysaccharide of Astragalus (Astragalan I or II) in immune and other pharmacological character.

EXAMPLE 4

Preparation of curde product of SDI II

Crude SDI II is extracted from as mentioned above herbs by ethanol and water. Proportion of herbs, for example, is as following (by weight):

|  | Weight Percent |
| --- | --- |
| Wang Qi | 30 to 80% |
| Ginseng | 30 to 80% |

The tissues of herbs were dried and powdered. 5 liters distallatory water was added 1 kg of dried powder. The solution was heated to boil and simmered for one hour after boiling. This water extraction was repeated two time. Combined and filtered. The filtrate was concentrated under reduced pressure to approximately 500 ml. Then 2,000 ml of 90% ethanol was added to 500 ml water solution. Stir. Stilled. Filtered. Residue and filtrat (A) was obtained. 1,000 ml 90% ethanol was added to residue. Extract. Filtered. Filtrate (B) was obtained.

Combined filtrate (A) with (B). The total filtrate was concentrated to syrup under reduced pressure distillation. Ethanol was recoved. Syrup dried under vacuum drying. Granulated to final powder. Weight of every capsule and table is about 200-500 mg. Crude-SDI II is similar to fine-SDI II in pharmacological property.

The following examples are related to pharmacological tests.

NOTES IN THE EXPLANATION OF PHARMACOLOGICAL EXPERIMENTS

The drugs, which as mentioned above (P. 3), are antimetabolites. According to the similar of chemical structure and pharmacological character of drug, above drugs can divede the following groups:
(a) AZC, AZU, AZT, AZCdR;
(b) DDA, DDC, DDI;
(c) CP, CC;
(d) Ara-C, Ara-A;
(e) other: Ribavirin (Rib), IDU, ACV, et al.

The first drug of every group to pharmacological experiments are selected from the drugs of every group.

Male mice weight 18-20 g were used in the experimetns. The dosage of SDI is 5-10 mg/kg injected intraperitoneally. The normal mice were injected with same volume of normal saline. These injections were repeated daily for 3-5 days. On the last say, both antiviral drug and antiviral drug+SDI group were injected interaperitoneally. The experimental procedure of all examples in mice is similar to the above procedures.

EXAMPLE 5

The effect of SDI II on Natural Killer Cells

Natural Killer (NK) Cells can destrou many viruse. NK cells may be important in limiting early spread of virus, also Natural Killer Cytotoxicity is effective antiviral agent. NK cell cytoxicity was tested by chromium release which assay using $^{51}$Cr-labelled YAC-1 or EAC cell line as targer cells. Tumors cells were maintained as stationary suspension and cultured in RPMI 1640 medium supplemented with 10% fetal calf serum. Spleen cells ($1-2 \times 10$/ml) were incubated in RPMI 1640 for 12 hours at 37° C. with $5 \times 10^5$ of $^{51}$Cr (as sodium chromate) labelled YAC-1 or EAC cells in volume of 1 ml plastic tuber under a 5% CO$_1$ humidified incubator. The effector cell to target cell (E:T) radio is 100:1. After the incubation the tuber were spun, the amount of $^{51}$Cr-released in 0.1 ml supernatant was counted by r-scintillation counter. Percent cytotoxicity was calculated from the following formula:

$$\% \text{ . Cytotoxicity} = \frac{\text{CPM (Test)} - \text{CPM (Spontaneous)}}{\text{CPM (Miximal)} - \text{CPM (Spontaneous)}} \times 100\%$$

The spontaneous release usually ranged from 8 to 15% of the maximum $^{51}$Cr released in controls.

TABLE 1

| | Normal | AZC (80 μg/ml) C | T | DDA (80 μg/ml) C | T | CP (80 μg/ml) C | T | Rib (80 μg/ml) C | T |
|---|---|---|---|---|---|---|---|---|---|
| % Cytotoxicity | 39.2 ± 3.2 | 11.2 ± 1.8 | 26.5 ± 2.1 | 18.0 ± 2.0 | 31.1 ± 2.9 | 20.7 ± 2.4 | 34.6 ± 7.0 | 22.3 ± 3.2 | 35.5 ± 5.8 |
| Number of sample | 12 | 12 | 12 | 12 | 12 | 12 | 12 | 12 | 12 |
| P | — | | <0.1 | | <0.1 | | <0.5 | | <0.1 |

C: Control - only antiviral drug
T: Treatment - antiviral drug + SDI II

EXAMPLE 6

The effects of SDI II on bone-marrow cells

Effects of SDI on hemopoietic system were investigated. The results showed that SDI (ip) could markedly improve the recovery rate of hemopoieses in treatment mice by antiviral drug.

With increased cells in bone-marrow (BMC), endogenous colunies in spleen and higher $^3$H-TdR uptake in marrow and spleen. It is found that SDI protect the stem cells of bone marrow in mice from the killing effect of antiviral drugs.

Pharmacological effects as illustrated by the following table: by means of the spleen colony assay the action of SDI II on bone marrow stem cells (CFU-S).

TABLE 2

| | Normal | AZC (80 μg/ml) C | T | DDA (80 μg/ml) C | T | CP (80 μg/ml) C | T | Ara-C (80 μg/ml) C | T | Rib (80 μg/ml) C | T |
|---|---|---|---|---|---|---|---|---|---|---|---|
| Mean CFU ± SD | 10.2 ± 0.82 | 3.1 ± 0.30 | 6.8 ± 0.90 | 4.2 ± 0.51 | 8.4 ± 0.90 | 4.0 ± 0.70 | 8.1 ± 0.98 | 3.8 ± 0.41 | 8.4 ± 0.95 | 4.2 ± 0.52 | 9.2 ± 0.90 |
| Number of sample | 10 | 10 | 10 | 10 | 10 | 10 | 10 | 10 | 10 | 10 | 10 |
| P | — | | <0.5 | | <0.5 | | <0.5 | | <0.5 | | <0.5 |

C: Control - only antiviral drug
T: Treatment - antiviral drug + SDI II

EXAMPLE 7

The effect of SDI II on lymphoblastoid transformation

Lymphoblastoid transformation test

1. Reagents and conditions for cell culture
   a. Culture media—RPMI 1640, madium 199 minimal essential medium (Eagle).
   b. 37° C. to maintain the pH of the medium at 7.31.
   c. Serum—generally 15-20% fetal bovine serum was incorporated.
   d. Gaseous phase 5% CO$_2$ in air;
   e. Cell concentration—generally $1-2 \times 10^6$/ml;
   f. Stimulants—20 μg/ml for phytoagglutinin containing polysaccharide (PHA-M) or 10 μg/ml for polysaccharide-free purified phytoagglutinin (PHA-P).
2. Measured by liquid scintillation
   a. The conditions of cell culture are same as above. $^3$H-TdR was added after 48 hours of incubation at a final concentration of 2 μCi/ml and continue the incubation for 24 hours.
   b. Wash the cells twice with cold normal saline and the erythrocytes were lysed by addition of distilled-water and equal volume of 3.6% NaCi was then added. The intact lymphocytes and add 2 ml of 10% trichloroacetic acid to precipitate the protein. Wash twice with normal saline. Add 2 ml of ethanol: ether (1:1) to wash once. 0.2 ml of formic acid was then added for digestion till the precipitate was dissolved.
   c. Add 4 ml of scintillation fluid to 0.1 ml of the final sample and count in a liquid scintillation counter.

The resulrs are listed in the following table:

TABLE 3

| | Normal | AZC (80 μg/ml) C | T | DDA (80 μg/ml) C | T | CP (80 μg/ml) C | T | Ara-C (80 μg/ml) C | T | Rib (80 μg/ml) C | T |
|---|---|---|---|---|---|---|---|---|---|---|---|
| CPM | 1340 ± 51 | 441 ± 57 | 1035 ± 129 | 502 ± 63 | 1055 ± 122 | 620 ± 58 | 1233 ± 69 | 654 ± 80 | 1209 ± 126 | 763 ± 95 | 1112 ± 140 |
| Number of sample | 10 | 10 | 10 | 10 | 10 | 10 | 10 | 10 | 10 | 10 | 10 |

TABLE 3-continued

| | Normal | AZC (80 μg/ml) | | DDA (80 μg/ml) | | CP (80 μg/ml) | | Ara-C (80 μg/ml) | | Rib (80 μg/ml) | |
|---|---|---|---|---|---|---|---|---|---|---|---|
| | | C | T | C | T | C | T | C | T | C | T |
| P | — | | <0.01 | | <0.1 | | <0.01 | | <0.1 | | <0.5 |

C: Control - only antiviral drug
T: Treatment - antiviral drug + SDI II

EXAMPLE 8

The effect of SDI II on white blood cells

Action of SDI II and antiviral drug on white blood cells was investigated by means of white blood cells assay. It was revealed that SDI II protect white blood cells from the killing effect of antiviral drugs. Time of treatment is 7 days. The results are listed below table:

EXAMPLE 9

The influence of SDI II on formation of rosette

1. Method
   a. Obtain venous blood in heparin (10 IU $ml^{-1}$) and perform a total and differential leucocyte count.
   b. Isolate lymphocyte fraction. Count vaiable lymphocytes calculate and record total yield. Adjust to $5 \times 10^5$ lymphocytes $ml^{-1}$.
   c. Wash sheep erythrocytes by centrifugation (400 g for 10 minutes at room temperature) and ajust to a 2.5% v/v suspension in PBS.
   d. Mix 0.1 ml of the lymphocyte suspension with 0.1 ml of sheep erythrocytes and centrifuge at 225 g for 5 minutes at room temperature.
   e. Incubate for 2 hours at 4° C.
   f. Add 50 μl of fetal bovine serum (FBS).
   g. Resuspend cell mixture by gently tapping the tube and pipette a sample into a haemocytomer.
   h. Count 200 lymphocytes and determine the percentage of cell with 3 or more erythrocytes attached. (Three are T lymphocytes).
   i. Calculate the absolute number of T lymphocytes $ml^{-1}$ of original blood.
2. The results are listed the following table:

TABLE 5

| | Normal | AZC (80 μg/ml) | | DDA (80 μg/ml) | | CP (80 μg/ml) | | Ara-C (80 μg/ml) | | Rib (80 μg/ml) | |
|---|---|---|---|---|---|---|---|---|---|---|---|
| | | C | T | C | T | C | T | C | T | C | T |
| Rate of formed rosette | 43.8 ± 2.0 | 19.8 ± 2.0 | 32.1 ± 6.3 | 22.4 ± 3.6 | 38.6 ± 5.0 | 20.7 ± 1.8 | 39.5 ± 4.1 | 23.7 ± 3.7 | 36.7 ± 5.3 | 28.7 ± 5.0 | 39.2 ± 4.6 |
| Number of sample | 12 | 12 | 12 | 12 | 12 | 12 | 12 | 12 | 12 | 12 | 12 |
| P | — | | <0.5 | | <0.5 | | <0.1 | | <0.5 | | <0.5 |

C: Control - only antiviral drug
T: Treatment - antiviral drug + SDI II

TABLE 4

| | Normal | AZC (80μg/ml) | | DDA (80 μg/ml) | | CP (80 μg/ml) | | Ara-C (80 μg/ml) | | Rib (80 μg/ml) | |
|---|---|---|---|---|---|---|---|---|---|---|---|
| | | C | T | C | T | C | T | C | T | C | T |
| White blood cells × $10^3$/$cm^3$ ± SD | 14.6 ± 2.1 | 3.8 ± 0.40 | 8.6 ± 1.0 | 4.2 ± 0.61 | 9.1 ± 2.1 | 5.3 ± 1.0 | 12.8 ± 2.4 | 4.2 ± 0.58 | 9.8 ± 9.6 | 4.9 ± 0.60 | 12.1 ± 1.8 |
| Number of sample | 10 | 9 | 9 | 9 | 9 | 9 | 9 | 9 | 9 | 9 | 9 |
| P | | | <0.1 | | <0.5 | | <0.5 | | <0.5 | | <0.5 |

C: Control - only antiviral drug
T: Treatment - antiviral drug + SDI II

EXAMPLE 10

The effect of SDI II on phagocytosis of peritoneal macrophage of mice

Method

Count the number of macrophanges in the peritoneal exudate of mice and adjust to $1 \times 10^7$ cell/ml with normal saline. Add 0.1 ml of the macrophage suspension. i.e. $1 \times 10^6$ cells to each well on the plastic plate for test. Lable the chick red blood cell with $^{51}$Cr. Suspend the labelled chick red blood cell and adjust to $1.5 \times 10^8$/ml, add 0.1 ml, i.e. $1.5 \times 10^7$, to each well. Incubate at 37° C. for 30 minutes. Wash thoughly to remove the free chick red blood cells. Count each well in a γ-counter.

TABLE 6

| | Normal | AZC (80 μg/ml) | | DDA (80 μg/ml) | | CP (80 μg/ml) | | Ara-C (80 μg/ml) | | Rib (80 μg/ml) | |
|---|---|---|---|---|---|---|---|---|---|---|---|
| | | C | T | C | T | C | T | C | T | C | T |
| CPM | 1089 ± 341 | 401 ± 51 | 812 ± 102 | 489 ± 64 | 795 ± 102 | 481 ± 44 | 802 ± 74 | 512 ± 63 | 895 ± 98 | 540 ± 62 | 980 ± 107 |
| Number of sample | 12 | 12 | 12 | 12 | 12 | 12 | 12 | 12 | 12 | 12 | 12 |
| P | — | | <0.5 | | <0.5 | | <0.5 | | <0.5 | | <0.5 |

C: Control - only antiviral drug
T: Treatment - antiviral drug + SDI II

EXAMPLE 11

Safety of composition

1. The acute $LD_{50}$ of fine composition was found to be 1872 mg/kg injection in abodominal cavity in mice.
2. $LD_{50}$ of crude composition: 7.1 g/kg injection in abodominal cavity in mice.
3. Each dose for an adult is 500-1000 mg. Using 50 kg as the average weight of an adult the dosage is 10-20 mg/kg, therefore, it is very safe.
4. As to subacut toxicity tests, a dosage corresponding to 50 times the clinical dose is administered continually for two months, and no side-effects have been observed. The electrocardiograms and functions of liver and the kidney have not been effected and no injuries whatever have been observed in the tissue slices of the heart, liver, spleen, lungs, kidneys and adrenal.

The preparation of composition is simple and can be accomplished by the extraction methods set forth above or any conventional methods for extracting the active ingredients. The novelty of the present invention resides in the mixture of the active ingredients in the specified proportions at invention and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsules, syrups, elixirs, and solutions for injection with specified ranges of composition.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by letters patent is set forth in the appended claims

1. A pharmaceutical composition for decreasing side effects of anti-viral drugs comprising:
   20-80 wt. % of polysaccharide of Wang Qi derived from a plant selected from the group consisting of *Astragalus membranceus* Bge, and *Astragalus chrysopterus* Bge; and
   20-80 wt. % of ginsenoside derived from a plant selected from the group consisting of *Panax quinquefolium* L and *Panax ginseng* C. A. Mey.

2. A method of reducing side effects of anti-viral drugs in humans suffering thereof comprising: administering to said humans an effective dosage of the pharmaceutical composition of claim 1.

* * * * *

UNITED STATES PATENT AND TRADEMARK OFFICE
CERTIFICATE OF CORRECTION

PATENT NO. : 5,071,839

DATED : Dec. 10, 1991

INVENTOR(S) : Yaguang Liu

It is certified that error appears in the above-identified patent and that said Letters Patent is hereby corrected as shown below:

On the title page:

Attorney, Agent or Firm -----CHENPATENTS

Signed and Sealed this

Ninth Day of March, 1993

*Attest:*

STEPHEN G. KUNIN

*Attesting Officer*      *Acting Commissioner of Patents and Trademarks*